United States Patent
Tempest et al.

(10) Patent No.: US 6,500,931 B1
(45) Date of Patent: Dec. 31, 2002

(54) HUMANIZED ANTIBODIES TO FC RECEPTORS FOR IMMUNOGLOBULIN G ON HUMAN MONONUCLEAR PHAGOCYTES

(75) Inventors: Philip R. Tempest, Royston; William J. Harris, Carnoustie; Frank J. Carr, Balmedie, all of (GB)

(73) Assignee: Medarex, Inc., Annandale, NJ (US)

( * ) Notice: Subject to any disclaimer, the term of this patent is extended or adjusted under 35 U.S.C. 154(b) by 0 days.

(21) Appl. No.: 08/435,516

(22) Filed: May 4, 1995

(30) Foreign Application Priority Data

Nov. 4, 1992 (GB) .............................................. 9223377

(51) Int. Cl.[7] .............................................. C12K 21/08
(52) U.S. Cl. .............................. 530/387.3; 530/388.22; 530/388.8; 530/388.85; 435/240.27
(58) Field of Search ........................ 530/387.3, 388.22, 530/388.8, 388.85; 435/240.27

(56) References Cited

U.S. PATENT DOCUMENTS

| | | | |
|---|---|---|---|
| 4,816,397 A | | 3/1989 | Boss et al. |
| 4,954,617 A | * | 9/1990 | Fanger et al. ................ 530/387 |
| 5,530,101 A | | 6/1996 | Queen et al. ................ 530/387.3 |
| 5,585,089 A | | 12/1996 | Queen et al. ............. 424/133.1 |
| 5,693,761 A | | 12/1997 | Queen et al. ............. 536/23.53 |
| 5,693,762 A | | 12/1997 | Queen et al. ............. 530/387.3 |

FOREIGN PATENT DOCUMENTS

| | | |
|---|---|---|
| EP | 0255249 A2 | 2/1988 |
| EP | 0340002 A1 | 11/1989 |
| GB | 2188638 | 10/1987 |
| WO | 9007861 * | 7/1990 |
| WO | WO9109967 * | 7/1991 |
| WO | WO 9211018 | 7/1992 |

OTHER PUBLICATIONS

Weiner Et Al. Cancer Res. S3:94–100, 1993.*
Songsivilai Et Al. Clin. Exp. Immunol. 79:315–321, 1990.*
Fanger Et Al., Critical Reviews in Immunology 12:101–124, 1992.*
Kabat, Sequences of Proteins of Immunological Interest, 4Th Ed 1987, USDHHS pp. 41, 63, 169,164.*
Fanger et al. (1992) Crit. Rev. Immunol. 12(3,4):101–124.*
Rudikoff et al Proc Natl Acad sci USA vol. 79 1979, 1982.*
Orlandi, Rosaria, et al., (1989), "Cloning Immunoglobulin Variable Domains for Expression by the Polymerase Chain Reaction", *Proc. Natl. Acad. Sci. USA*, 86, pp. 3833–3837.
Saragovi, Horacio U., et al., ((1991), "Design and Synthesis of a Mimetic from an Antibody Complementarity–Determining Region", *Science*, 53, pp. 792–795.
PCT International Search Report, Dated Feb. 21, 1994.
Lewis, Alan P., et al., (1991), "Immunoglobulin Complementarity–Determining Region Grafting by Recombinant Polymerase Chain Reaction to Generate Humanised Monodlonal Antibodies", *Gene*, 101, No. 2, pp. 297–302.
Riechmann, Lutz, et al., (1988), "Reshaping Human Antibodies for Therapy", *Nature*, 332, pp. 323–327.

* cited by examiner

*Primary Examiner*—Geetha P. Bansal
(74) *Attorney, Agent, or Firm*—Lahive & Cockfield, LLP; Jane E. Remillard, Esq.; Peter W. Dini

(57) ABSTRACT

Humanized antibodies are described which are specific to an Fc receptor (FcR). The humanized antibodies have at least a portion of a complementarity determining region (CDR) derived from a non-human antibody, e.g., murine, with the remaining portions being human in origin. The humanized antibodies can be used therapeutically as is or formulated as bifunctional molecules or immunotoxins.

20 Claims, 3 Drawing Sheets

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
       (A) LENGTH: 120 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 1:

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Ile Phe Ser Asp Asn
            20                  25                  30

Tyr Met Tyr Trp Val Arg Gln Pro Pro Gly Arg Gly Leu Glu Trp Ile
        35                  40                  45

Gly Thr Ile Ser Asp Gly Gly Ser Tyr Thr Tyr Tyr Pro Asp Ser Val
    50                  55                  60

Lys Gly Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Gly Tyr Tyr Arg Tyr Glu Gly Ala Met Asp Tyr Trp Gly Gln
                100                 105                 110

Gly Ser Leu Val Thr Val Ser Ser
            115                 120
```

(2) INFORMATION FOR SEQ ID NO: 2:

(i) SEQUENCE CHARACTERISTICS:
       (A) LENGTH: 120 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO: 2:

```
Glu Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Asp Asn
            20                  25                  30

Tyr Met Tyr Trp Val Arg Gln Ala Pro Gly Lys Gly Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Tyr Tyr Arg Tyr Glu Gly Ala Met Asp Tyr Trp Gly Gln
                100                 105                 110
```

```
Gly Thr Pro Val Thr Val Ser Ser
        115                 120

(2) INFORMATION FOR SEQ ID NO: 3:

(i) SEQUENCE CHARACTERISTICS:
        (A) LENGTH: 120 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 3:

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Ile Phe Ser Asp Asn
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Tyr Thr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Ile Tyr Tyr Cys
                85                  90                  95

Ala Arg Gly Tyr Tyr Arg Tyr Glu Gly Ala Met Asp Tyr Trp Gly Gln
            100                 105                 110

Gly Thr Ser Val Thr Val Ser Ser
        115                 120

(2) INFORMATION FOR SEQ ID NO: 4:

(i) SEQUENCE CHARACTERISTICS:
        (A) LENGTH: 112 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

Asp Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
            20                  25                  30

Ser Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gln Gly Thr Lys Val Glu Ile Lys
            100                 105                 110

(2) INFORMATION FOR SEQ ID NO: 5:
```

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 5:

GGAAGCTTAG ACAGATGGGG GTGTCGTTTT G                            31

(2) INFORMATION FOR SEQ ID NO: 6:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO: 6:

Thr Gly Ala Gly Gly Ala Gly Ala Cys Gly Gly Thr Gly Ala Cys Cys
1               5                   10                  15

Gly Thr Gly Gly Thr Cys Cys Cys Thr Thr Gly Gly Cys Cys Cys Cys
            20                  25                  30

Ala Gly (2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

AGGTSMARCT GCAGSAGTCW GG                                      22

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

TGGAATTCAT GGRATGGAGC TGGRTCWTBH TCTT                         34

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TGGAATTCAT GRACTTCDGG YTCAACTKRR TTT                          33

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
GGAAGCTTGA AGATGGATAC AGTTGGTGCA GC                                  32
```

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
GACATTCAGC TGACCCAGTC TCCA                                           24
```

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
TTGAATTCGG TGCCAGAKCW SAHATYGTKA TG                                  32
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
TTGAATTCGG TGGCAGAKCW SAHATYGTKC TC                                  32
```

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
TTGAATTCGG AGCTGATGGG AACATTGTAA TG                                  32
```

(2) INFORMATION FOR SEQ ID NO: 15:

(i) SEQUENCE CHARACTERISTICS:

(A) LENGTH: 61 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 15:

```
TGCCTGTCTC ACCCAATACA TGTAATTGTC ACTGAAATGA AGCCAGACGM GGAGCGGACA    60

G                                                                   61
```

(2) INFORMATION FOR SEQ ID NO: 16:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
TGTAAATCTT CCCTTCACAC TGTCTGGATA GTAGGTGTAA CTACCACCAT CACTAATGGT    60

TGCAACCCAC TCAGG                                                    75
```

(2) INFORMATION FOR SEQ ID NO: 17:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
GGGGTCCCTT GGCCCCAGTA GTCCATAGCC CCCTCGTACC TATAGTAGCC TCTTGCACAA    60

AAATAGA                                                             67
```

(2) INFORMATION FOR SEQ ID NO: 18:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

```
TGGCTGTCTC ACCCAATACA TGTAATTGTC GCTGAAAATG AAGCCAGACA CGGTGCAGGT    60

CAGGCTCA                                                            68
```

(2) INFORMATION FOR SEQ ID NO: 19:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
TTGCTGGTGT CTCTCAGCAT TGTCACTCTC CCCTTCACAC TGTCTGGATA GTAGGTGTAA    60
```

```
CTACCACCAT CACTAATGGT TCCAATCCAC TCAA                                        94
```

(2) INFORMATION FOR SEQ ID NO: 20:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

```
AGACGGTGAC CAAGGACCCT TGGCCCCAGT AGTCCATAGC CCCCTCGTAC CTATAGTAGC            60

CTCTTGCACA ATAATAG                                                          77
```

(2) INFORMATION FOR SEQ ID NO: 21:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

```
CTTCTGCTGG TACCAGGCCA AGTAGTTCTT CTGATTTGAA CTGTATAAAA CACTTTGACT            60

GGACTTACAG GTGATGGTCA C                                                     81
```

(2) INFORMATION FOR SEQ ID NO: 22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

```
GCTTGGCACA CCAGATTCCC TAGTGGATGC CCAGTAGATC AGCAG                            45
```

(2) INFORMATION FOR SEQ ID NO: 23:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

```
CCTTGGCCGA ACGTCCACGA GGAGAGGTAT TGATGGCAGT AGTAGGTGG                        49
```

(2) INFORMATION FOR SEQ ID NO: 24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

```
GTAAAACGAC GGCCAGT                                                              17

(2) INFORMATION FOR SEQ ID NO: 25:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 25:

AACAGCTATG ACCATG                                                               16

(2) INFORMATION FOR SEQ ID NO: 26:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 26:

TTTACAATAT CGAGACAACA GCAA                                                      24

(2) INFORMATION FOR SEQ ID NO: 27:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 27:

TTGCTGTTGT CTCTCGATTG TAAA                                                      24

(2) INFORMATION FOR SEQ ID NO: 28:

(i) SEQUENCE CHARACTERISTICS:
          (A) LENGTH: 112 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO: 28:

Asn Ile Val Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

-continued

```
Ile Ser Ser Val Gln Ala Glu Asp Leu Ala Val Tyr Tyr Cys His Gln
                85                  90                  95

Tyr Leu Ser Ser Trp Thr Phe Gly Gly Gly Thr Lys Leu Glu Ile Lys
            100                 105                 110
```

HUMANIZED ANTIBODIES TO FC RECEPTORS FOR IMMUNOGLOBULIN G ON HUMAN MONONUCLEAR PHAGOCYTES

BACKGROUND

Human Fcγ receptors (FcγR) (reviewed in Fanger, M. W., et al. (1989) Immunology Today 10:92–99), of which there are three structurally and functionally distinct types (i.e., FcγRI, FcγRII and FcγRIII), are well-characterized cell surface glycoproteins that mediate phagocytosis or antibody-dependent cell cytotoxicity (ADCC) of immunoglobulin G (IgG) opsonized targets. Antibodies have been made which are directed towards FcγR for various purposes, e.g., targeting of immunotoxins to a particular target cell type, or radioimaging a particular target cell type. The antibodies typically have been murine antibodies.

Murine monoclonal antibodies are sometimes desirable for human therapeutic applications because the antibodies can be purified in large quantities and are free of contamination by human pathogens such as the hepatitis or human immunodeficiency virus. Murine monoclonal antibodies have been used in some human therapies, however, results have not always been desirable due to the development of an immune response to the "foreign" murine proteins. The immune response has been termed a human anti-mouse antibody or HAMA response (Schroff, R. et al. (1985), Cancer Res., 45, 879–885) and is a condition which causes serum sickness in humans and results in rapid clearance of the murine antibodies from an individual's circulation. The immune response in humans has been shown to be against both the variable and the constant regions of the murine immunoglobulin.

Recombinant DNA technology has provided the ability to alter antibodies by substituting specific immunoglobulin regions from one species with immunoglobulin regions from another species. Neuberger et al. (Patent Cooperation Treaty Patent Application No. PCT/GB85/00392) describes a process whereby the complementary heavy and light chain variable domains of an Ig molecule from one species may be combined with the complementary heavy and light chain Ig constant domains from another species. This process may be used to substitute the murine constant region domains to create a "chimeric" antibody which may be used for human therapy. A chimeric antibody produced as described by Neuberger et al. would have the advantage of having the human Fc region for efficient stimulation of antibody mediated effector functions, such as complement fixation, but would still have the potential to elicit an immune response in humans against the murine ("foreign") variable regions.

Winter (British Patent Application Number GB2188538A) describes a process for altering antibodies by substituting the complementarity determining regions (CDRs) with those from another species. This process may be used to substitute the CDRs from the murine variable region domains of a monoclonal antibody with desirable binding properties (for instance to a human pathogen) into human heavy and light chain Ig variable region domains. These altered Ig variable regions may then be combined with human Ig constant regions to create antibodies which are totally human in composition except for the substituted murine CDRs. The "reshaped" or "humanized" antibodies described by Winter elicit a considerably reduced immune response in humans compared to chimeric antibodies because of the considerably less murine components. Further, the half life of the altered antibodies in circulation should approach that of natural human antibodies. However, as stated by Winter, merely replacing the CDRs with complementary CDRs from another antibody which is specific for an antigen such as a viral or bacterial protein, does not always result in an altered antibody which retains the desired binding capacity. In practice, some amino acids in the framework of the antibody variable region interact with the amino acid residues that make up the CDRs so that amino acid substitutions into the human Ig variable regions are likely to be required to restore antigen binding.

SUMMARY OF THE INVENTION

The present invention pertains to humanized antibodies specific to an Fc receptor (FcR). The humanized antibodies have at least a portion of a complementarity determining region (CDR) derived from a non-human antibody, e.g., murine, with the remaining portions being human in origin. The use of humanized antibodies rather than murine antibodies in human therapy should alleviate some of the problems associated with the use of some murine monoclonal antibodies because only the substituted CDRs will be foreign to a human host's immune system.

The present invention farther pertains to the use of humanized antibodies specific to an FcR as components in heteroantibodies, bifunctional antibodies, or immunotoxins. The humanized antibody specific to an FcR may be used in the same manner and for the same purpose as its corresponding murine counterpart. For example, the humanized anti-Fc receptor antibody of this invention can be used to treat cancer, allergies, and infectious and autoimmune diseases. Diagnostic applications of the antibodies include their use in assays for FcRI levels and assays for substances that influence FcR levels.

DETAILED DESCRIPTION

Figure 1:
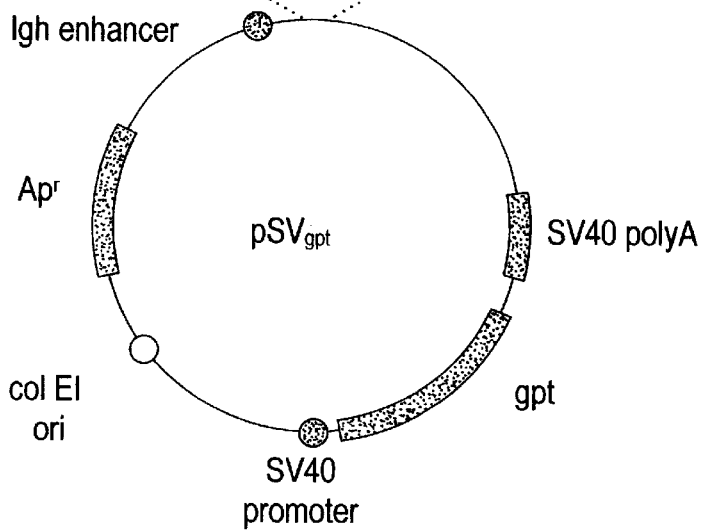
FIG. 1 depicts the vector used for expression of the humanized or chimeric 022 heavy chain gene.

The present invention pertains to a humanized antibody specific for an Fc receptor. The humanized antibody is made up of a human antibody having at least a portion of a complementarity determining region (CDR) derived from a non-human antibody. The portion is selected to provide specificity of the humanized antibody for a human Fc receptor. The humanized antibody has CDRs derived from a non-human antibody and the remaining portions of the antibody molecule are human.

The antibody may be a complete antibody molecule having full length heavy and light chains or any fragment thereof, e.g., Fab or (Fab')$_2$ fragment. The antibody further may be a light chain or heavy chain dimer, or any minimal fragment thereof such as a Fv or a single chain construct as described in Ladner et al. (U.S. Pat. No. 4,946,778, issued Aug. 7, 1990), the contents of which is expressly incorporated by reference.

The human antibody of the present invention may be any human antibody capable of retaining non-human CDRs. The preferred human antibody is derived from known proteins NEWM and KOL for heavy chain variable regions (VHs)

and REI for Ig kappa chain, variable regions (VKs). These proteins are described in detail in the examples below.

"Complementarity determining region" (CDR) is an art recognized term and the technique used for locating the CDRs within the described sequences also is conventional.

The portion of the non-human CDR inserted into the human antibody is selected to be sufficient for allowing binding of the humanized antibody to the Fc receptor. A sufficient portion may be selected by inserting a portion of the CDR into the human antibody and testing the binding capacity of the created humanized antibody using the enzyme linked immunosorbent assay (ELISA) described in the examples below.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor. The exemplified non-human CDR is derived from a murine antibody, particularly the CDR is derived from a monoclonal antibody (mab), mab 22. The mab 22 antibody is specific to the Fc receptor and further is described in U.S. Patent application Ser. No. 07/151,450, filed on Feb. 2, 1988, and in Fanger et al. (U.S. Pat. No. 4,954,617, issued Sep. 4, 1988). The entire contents of the aforementioned pending application and issued patent are expressly incorporated by reference.

The CDRs are derived from a non-human antibody specific for a human Fc receptor. The CDRs can be derived from known Fc receptor antibodies such as those discussed in the Fanger et al. patent application and issued patent cited above (hereinafter Fanger et al.). The CDR may be derived from an antibody which binds to the Fc receptor at a site which is not blocked by human immunoglobulin G. The antibody also may be specific for the high affinity Fc receptor for human immunoglobulin G. Examples of antibodies from which the non-human CDRs may be derived are mab 32, mab 22, mab 44, mab 62, mab 197 and anti-FcRI antibody 62. The humanized mab 22 antibody producing cell line has been deposited at the American Type Culture Collection on Nov. 4, 1992 under the designation HA022CL1 and has the accession no. CRL 11177.

The present invention also pertains to humanized bifunctional molecules (i.e. molecules having two distinct binding specificities, at least one of which is humanized). For example, a bispecific molecule can have a binding specificity for a pathogen (e.g. virus, bacteria, fungi), pathogen infected cell, cancer (e.g. breast, ovarian, prostate, etc.) or other unwanted cell in a host and a binding specificity for an Fcγ receptor on an effector cell. A bispecific molecule may be comprised of two antibodies, in which event it is known as a "heteroantibody". Procedures for generating bispecific molecules such as 520C9×H22, a humanized bispecific molecule against the HER 2/neu antigen of breast cancer cells is described in the attached Example 2. A humanized antigen binding region for an Fc receptor may be derived from a humanized anti-Fc receptor antibody as described above. Bifunctional molecules having an antibody portion specific for an Fc receptor are described in detail by Fanger et al.

It should be understood that the humanized antibodies of the present invention may be used in the same manner, e.g., as components of immunotoxins or heteroantibodies, as their corresponding non-humanized counterparts described by Fanger et al. The humanized antibodies further share the same utilities as their non-humanized counterparts. All aspects of the teachings of the Fanger et al. application and patent are incorporated by reference.

The humanized antibody of the present invention may be made by any method capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in the examples below.

The humanized antibody of the present invention may be made as described in the brief explanation below. A detailed method for production is set forth in the examples. It should be understood that one of ordinary skill in the art may be able to substitute known conventional techniques for those described below for the purpose of achieving the same result. The humanized antibodies of the present invention may be produced by the following process:

(a) constructing, by conventional techniques, an expression vector containing an operon with a DNA sequence encoding an antibody heavy chain in which the CDRs and such minimal portions of the variable domain framework region that are required to retain antibody binding specificity are derived from a non-human immunoglobulin, and the remaining parts of the antibody chain are derived from a human immunoglobulin, thereby producing the vector of the invention;

(b) constructing, by conventional techniques, an expression vector containing an operon with a DNA sequence encoding a complementary antibody light chain in which the CDRs and such minimal portions of the variable domain framework region that are required to retain donor antibody binding specificity are derived from a non-human immunoglobulin, and the remaining parts of the antibody chain are derived from a human immunoglobulin, thereby producing the vector of the invention;

(c) transfecting the expression vectors into a host cell by conventional techniques to produce the transfected host cell of the invention; and (d) culturing the transfected cell by conventional techniques to produce the altered antibody of the invention.

The host cell may be cotransfected with the two vectors of the invention, the first vector containing an operon encoding a light chain derived polypeptide and the second vector containing an operon encoding a heavy chain derived polypeptide. The two vectors contain different selectable markers, but otherwise, apart from the antibody heavy and light chain coding sequences, are preferably identical, to ensure, as far as possible, equal expression of the heavy and light chain polypeptides. Alternatively, a single vector may be used, the vector including the sequences encoding both the light and the heavy chain polypeptides. The coding sequences for the light and heavy chains may comprise cDNA or genomic DNA or both.

The host cell used to express the altered antibody of the invention may be either a bacterial cell such as *Escherichia coli*, or a eukaryotic cell. In particular a mammalian cell of a well defined type for this purpose, such as a myeloma cell or a Chinese hamster ovary cell may be used.

The general methods by which the vectors of the invention may be constructed, transfection methods required to produce the host cell of the invention and culture methods required to produce the antibody of the invention from such host cells are all conventional techniques. Likewise, once produced, the humanized antibodies of the invention may be purified according to standard procedures of the art, including cross-flow filtration, ammonium sulphate precipitation, affinity column chromatography, gel electrophoresis and the like.

It should be understood that the humanized antibodies of this invention perform in a manner which is the same or similar to that of the non-humanized versions of the same antibodies. It also is noted that the humanized antibodies of this invention may be used for the design and synthesis of either peptide or non-peptide compounds (mimetics) which would be useful for the same therapy as the antibody (Saragobi et al., *Science* 253:792–795 (1991)), the contents of which is expressly incorporated by reference.

The following examples are provided as a further illustration of the present invention and should in no way be construed as being limiting.

EXAMPLES

In the following examples all necessary restriction and modification enzymes, plasmids and other reagents and materials were obtained from commercial sources unless otherwise indicated.

In the following examples, unless otherwise indicated, all general recombinant DNA methodology was performed as described in "Molecular Cloning, A Laboratory Manual" (1982) Eds T. Maniatis et al., published by Cold Spring Harbor Laboratory Press, Cold Spring Harbor, N.Y., the contents of which is expressly incorporated by reference.

In the following examples the following abbreviations were employed:

| | |
|---|---|
| dCTP | deoxycytidine triphosphate |
| dATP | deoxyadenosine triphosphate |
| dGTP | deoxyguanosine triphosphate |
| dTTP | deoxythymidine triphosphate |
| DTT | dithiothreitol |
| C | cytosine |
| A | adenine |
| G | guanine |
| T | thymine |
| PBS | phosphate buffered saline |
| PBST | phosphate buffered saline containing 0.05% Tween 20 (pH 7.5) |

Example 1

Production of Humanized Antibodies Specific for an Fc Receptor

The source of the donor CDRs used to prepare the humanized antibody was a murine monoclonal antibody, mab 22, which is specific for the Fc receptor. A mab 22 hybridoma cell line (022WCL-1) was established. Cytoplasmic RNA was prepared from the mab 22 cell line using the method described by Favoloro et al. (*Methods in Enzymology* 65, 718–749 (1980)), the contents of which is expressly incorporated by reference. The cDNA was synthesized using IgGI and kappa constant region primers. The primer CG1FOR was used for the heavy chain variable (VH) region and the primer CK2FOR was used for the Ig kappa chain variable region (VK). The cDNA synthesis reactions mixtures consisted of 1 $\mu$g RNA, 0.5 $\mu$M CG1FOR or CK2FOR, 250 $\mu$M each of dATP, dCTP, dGTP, and dTTP, 50 mM Tris HCl (pH 7.5), 75 mM KCl, 10 mM dithiothreitol, 3 mM MgCl$_2$ and 20$\mu$ RNA guard (sold by Pharmacia, Milton Keynes, U.K.) in a total volume of 50 ti. The samples were heated at 72° C. for two minutes and slowly cooled to 37° C. Murine moloney leukemia virus reverse transcriptase (100 $\mu$l—sold by Life Technologies, Paisley, U.K.) was added to the samples and the transcriptase containing samples were incubated at 42° C. for sixty minutes.

VH and VK cDNAs were then amplified using the polymerase chain reaction (PCR) as described by Saiki et al. (*Science* 239, 487–491 (1988)), the contents of which is expressly incorporated by reference. The primers used in the above steps were as follows:

CG1FOR (SEQ ID NO:5) 5' GG AAGCTTAGACAGATGGGGGTGTCGTTTTG 3'

VH1FOR (SEQ ID NO:6) 5' TGAGGAGAC GGTGACCGTGGTCCCTTGGCCCCAG 3'

VH1BACK (SEQ ID NO:7) 5' AGGTSMAR CTGCAGSAGTCWGG 3'

SH1BACK (SEQ ID NO:8) 5' TG GAATTCATGGRATGGAGCTGGRTCWTBHTCTT 3'

SH2BACK (SEQ ID NO:9) 5' TG GAATTCATGRACTTCDGGYTCAACTKRRTTT 3'

CK2 FOR (SEQ ID NO:10) 5' GG AAGCTTGAAGATGGATACAGTTGGTGCAGC 3'

VK1BACK (SEQ ID NO:11) 5' GACATT CAGCTGACCCAGTCTCCA 3'

VK5BACK (SEQ ID NO:12) 5' TT GAATTCGGTGCCAGAKCWSAHATYGTKATG 3'

VK6BACK (SEQ ID NO:13) 5' TT GAATTCGGTGGCAGAKCWSAHATYGTKCTC 3'

VK7BACK (SEQ ID NO:14) 5' TT GAATTCGGAGCTGATGGGAACATTGTAATG 3'

Restriction sites incorporated in primers to facilitate cloning are underlined.

The PCR amplification of murine Ig DNA was conducted using the methodology described by Orlandi et al. (*Proc. Natl. Acad. Sci USA* 86, 3833–3838 (1989), the contents of which is expressly incorporated by reference. The DNA/primer mixtures consisted of RNA/cDNA hybrid (10 $\mu$l) and 25 pmol each of CG1FOR and SH1BACK or SH2BACK for PCR amplification of VH. The DNA/primer mixtures consisted of RNA/cDNA hybrid (10 $\mu$l) and 25 pmol each of CK2 FOR and VK1BACK, VK5BACK, VK6BACK, VK7BACK for PCR amplification of VK. dATP, dCTP, dGTP and dTTP (250 $\mu$M each), 10 mM Tris HCl (pH 8.3), 60 mM KCl, 1.5 mM MgCl$_2$, 0.01% (w/v) gelatin, 0.01% (v/v) Tween 20, 0.01% (v/v) NP40 and 2.5$\mu$ Amplitaq (sold by Cetus, Beaconsfield, U.K.) were added to the samples in a final volume of 50 $\mu$l. The samples were subjected to 25–30 thermal cycles of PCR at 94° C. for thirty seconds, 55° C. for thirty seconds, 72° C. for one minute and a final cycle at 72° C. for five minutes.

The amplified VH and VK DNAs were run on a low melting point agarose gel and purified by Elutip-d column chromatography (sold by Schleicher and Schueell, Anderman, Walton, U.K.) for cloning and sequencing. The purified VH DNAs were cut with Eco I or Pst I and Hind III and cloned into M13mp18 and mp19 (sold by Pharmacia, Milton Keynes, U.K.). The purified VK DNAs were cut with Pvu II or Eco I and Hind III and cloned into M13mp18 and mp19. For general cloning methodologies see Sambrook et al. (*Molecular Cloning: A Laboratory Manual*, Cold Spring Harbor Laboratory, Cold Spring Harbor, N.Y. (1989)), the contents of which are expressly incorporated by reference.

The resulting collection of clones were sequenced by the dideoxy method using T7 DNA polymerase (sold by Pharmacia, Milton Keynes, U.K.) as described by Sanger et al. (*Proc. Natl. Acad. Sci. USA* 74, 5463–5467, (1979)), the contents of which are expressly incorporated by reference.

From the sequences of the 022 VH and VR domains the CDR sequences were determined with reference to the database of Kabat et al. ("Sequences of Proteins of Immunological Interest" US Department of Health and Human Services, US Government Printing Office), the contents of which is expressly incorporated by reference, and utilizing computer assisted alignment with other VH and VK sequences. The VH sequence is shown in SEQ ID NO:1. The VK sequence is shown in SEQ ID NO:4.

Transfer of the murine 022 CDRs to human frameworks was achieved by oligonucleotide site-directed mutagenesis as described by Nakamye et al. (*Nucleic Acids Res* 14, 9679–9687 (1986)), the contents of which is expressly incorporated by reference. The primers used were as follows:

KLVHCDR1 (SEQ ID NO:15): 5' TGCCTGTCTCAC-CCAATACATGTAA TTGTCACTGAAATGAAGC-CAGACGMGGAGCGGACAG

KLVHCDR2 (SEQ ID NO:16): 5' TGTAAATCTTCCCT-TCACACTGTCTGGATAGTA GGTGTAACTAC-CACCATCACTAATGGTTGCAACCCACTCAGG

KLVHCDR3 (SEQ ID NO:17): 5' GGGGTCCCTTGGC-CCCAGTAGTCCATAGC CCCCTCGTACCTATAG-TAGCCTCTTGCACAAAAATAGA

NMVHCDR1 (SEQ ID NO:18): 5' TGGCTGTCTCAC-CCAATACATGTAATTGT CGCTGAAAATGAAGC-CAGACACGGTGCAGGTCAGGCTCA

NMVHCDR2(SEQ ID NO:19): 5' TTGCTGGT-GTCTCTCAGCATTGTCACTCTC CCCTTCA-CACTGTCTGGATAGTAGGTGTAACTACCACCA TCACTAATGGTTCCAATCCACTCAA

NMVHCDR3 (SEQ ID NO:20): 5' AGACGGTGAC-CAAGGACCCTTGGCCCCAG TAGTCCATAGC-CCCCTCGTACCTATAGTAGCCTCTTGCA-CAATAATAG

HuVKCDR1 (SEQ ID NO:21): 5' CTTCTGCTGGTAC-CAGGCCAAGTAGTTCTTC TGATTTGAACTG-TATAAAACACTTTGACTGGACTTACAG-GTGATGGTCAC

HuVKCDR2 (SEQ ID NO:22): 5' GCTTGGCACACCA-GATTCCCTAGTGGATG CCCAGTAGATCAGCAG

HuVKCDR3 (SEQ ID NO:23): 5' CCTTGGC-CGAACGTCCACGAGGAGAGGTAT TGATG-GCAGTAGTAGGTGG

The primer for NMVHCDR1 was extended to include a change of NEWM residues Ser 27 Thr 28 to Phe 27 Ile 28. The primer for NMVHCDR2 was extended to include a change of NEWM residue Val 71 to Arg 71.

The DNA templates used for mutagenesis of VHs comprised human framework regions from the crystallographically solved protein NEW described by Saul et al. (*J. Biol. Chem.* 53, 585–597 (1978)) or KOL described by Schmidt et al. (*Z. Physical Chem.* 364, 713–747 (1983)). The DNA templates used for mutagenesis of VKs comprised human framework regions from the crystallographically solved protein REI described by Epp et al. (*Eur. J. Biochem.* 45, 513–524 (1974)). The contents of each of the aforementioned references are expressly incorporated by reference.

M13 based templated M13 VHPCR1 (for NEWMVH), M13 VHPCR2 (for KOLVH) and M13 VKPCR2 (for REIVK) comprising human frameworks with irrelevant CDRs were prepared as described by Riechmann et al. (*Nature* 332, 323–327 (1988)), the contents of which are expressly incorporated by reference. Oligonucleotide site-directed mutagenesis was carried out using the following protocol. A 5-fold molar excess of each phosphorylated mutagenic oligonucleotide was added along with the universal M13 sequencing primer (5'-GTAAAACGACGGCCAGT) (SEQ ID NO:24). All of the primers were annealed in 20 µl 0.1 M TrisHCl (pH8.0) and 10 mM MgCl$_2$ by heating to 70–85° C. for two minutes and slowly cooling to room temperature. 10 mM DTT, 1 mM ATP, 40 µM each of dATP, dCTP, dGTP and dTTP, 2.5µ T7 DNA polymerase (sold by United States Biochemicals) and 0.5µ T4DNA ligase (sold by Life Technologies, Paisley, U.K.) was added to the annealed DNA in a reaction volume of 30 µl and incubated at 22°–37° C. for one to two hours. The newly extended and ligated strand was preferentially amplified over the parental strand in a thermostable DNA polymerase directed reaction using the M13 reverse sequencing primer (5' AACAGCTATGACCATG) (SEQ ID NO:25). The reverse sequencing primer is not complementary to the parental strand. The reaction mixture of 50 µl contained 1 µl extension/ligation product, 25 pmol M13 reverse sequencing primer, 250 µM each of dATP, dCTP, dGTP and dTTP, 1µ Vent DNA polymerase (sold by New England Biolabs, Bishop's Stortford, U.K.) or 2.5µ Amplitaq (sold by Cetus, Beaconsfield, U.K.) in the appropriate buffer supplied by the enzyme manufacturer and was subjected to thirty thermal cycles of 94° C., 30 s, 55° C., 30 s, 75° or 72° C., 90 s; ending with 5 min at 72° C. A 4 µl aliquot of this sample was then amplified by PCR using both M13 universal and reverse sequencing primers in a reaction mixture of 50 µl containing 25 pmol of each primer, 250 µM each of dATP, dCTP, dGTP and dTTP, 2.5µ Amplitaq (Cetus) in the buffer supplied by the enzyme manufacturer. Amplified DNAs were digested with HindIII and BamHI and cloned into M13 mp19 and sequenced.

Mutagenesis of M13VHPCR2 KOL VH residue Leu71 to Arg71 was by the overlap/extension PCR method of Ho et al. (*Gene*, 77, 51–55 (1989)), the contents of which is expressly incorporated by reference. The overlapping oligonucleotides used were 5'-TTTACAATATCGAGACAACAGCAA (SEQ ID NO:26) and 5'-TTGCTGTTGTCTCTCGATTGTAAA (SEQ ID NO:27).

Figure 2:
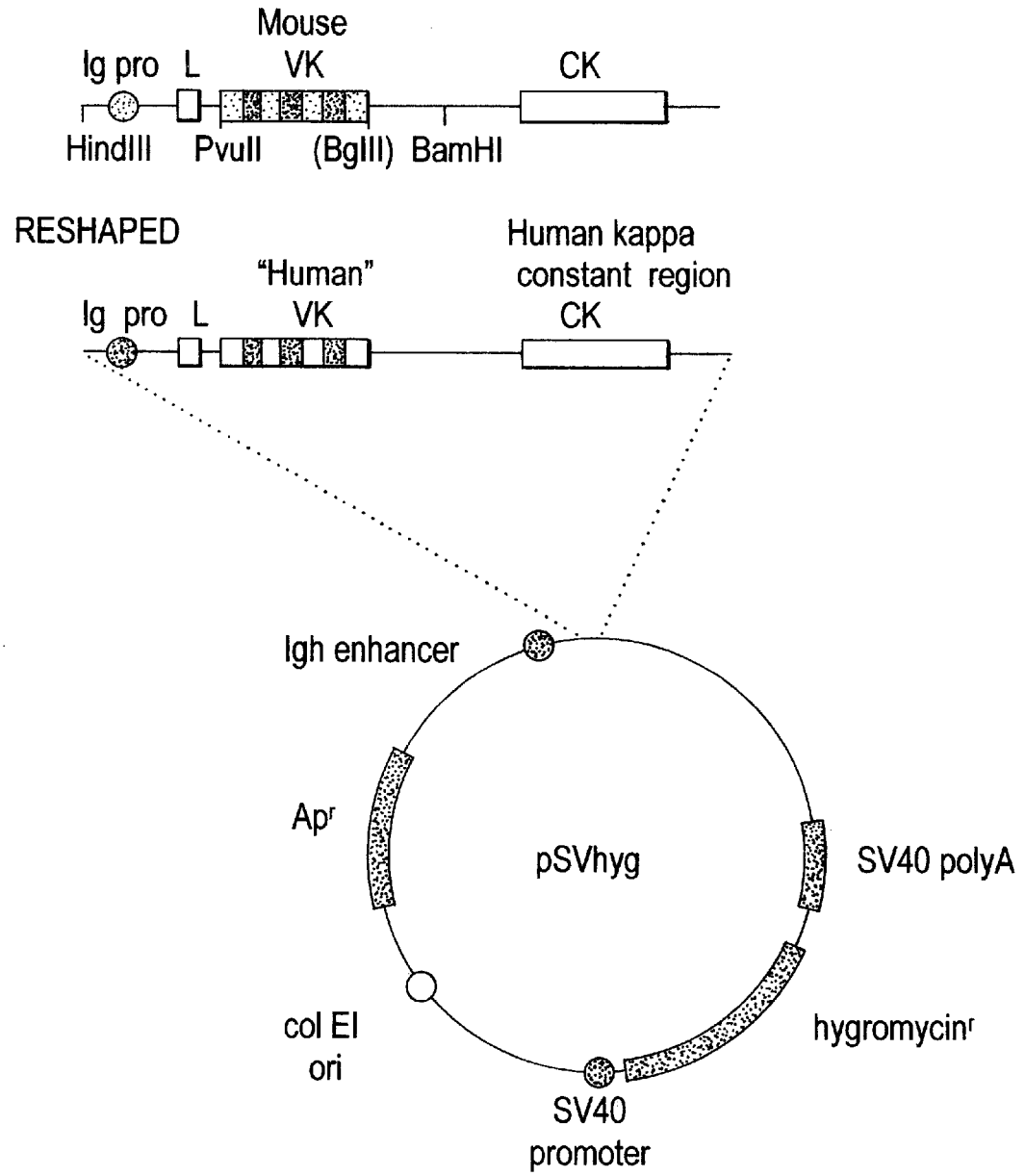
FIG. 2 depicts the vector used for expression of the humanized or chimeric 022 kappa chain gene.

The amino acid sequences of the humanized antibodies were compared to the known murine antibodies as shown in FIGS. 1 and 2. The CDR replaced VH and VK genes were cloned into expression vectors pSVgpt and pSVhyg as shown in FIGS. 1 and 2 as described by Orlandi et al. (cited supra). The CDR replaced NEWMVH and KOLVH genes together with the Ig heavy chain promoter, appropriate splice sites and signal peptide sequences were excised from M13 by digestion with HindII and BamHI and cloned into the pSVgpt expression vector containing the murine Ig heavy chain enchancer, the gpt gene for selection in mammalian cells and genes for replication and selection in *E. coli*. The plasmid also contains a human IgGI constant region as described by Takahashi et al. (*Cell* 29, 671–675 (1982)). The construction of the kappa chain expression vector was essentially the same except that the gpt gene was replaced by the hygromycin resistance gene and contains a human kappa constant region (Hieter et al., *Cell* 22, 197–207 (1980)). The contents of each of the aforementioned references are expressly incorporated by reference.

Approximately 5 µg of each heavy chain expression vector and 10 µg of the kappa chain expression vector were digested with PvuI. The DNAs were mixed together, ethanol precipitated and dissolved in 25 µl water. Approximately 5–10×10⁶ NSO cells (from European Collection of Animal Cell Cultures, Porton Down, U.K.) were grown to semi-confluency in Dulbecco's modified Eagle's medium (DMEM) plus 10% fetal calf serum (Myoclone plus, Gibco, Paisley, Scotland), harvested by centrifugation and resuspended in 0.5 ml DMEM together with the digested DNA in a cuvette. After five minutes in ice, the cells were given a single pulse of 170 V at 960 µF (Gene-Pulser, Bio-Rad, Richmond, Calif.) and left in ice for a further twenty minutes. The cells were then put into 20 ml DMEM+ supplemented with 10% FCS and allowed to recover for twenty-four to forty-eight hours. After this time, the cells were distributed into a 24-well plate and selective medium was applied (DMEM, 10% FCS, 0.8 µg/ml mycophenolic acid and 250 µg/ml xanthine). After three to four days, the medium and dead cells were removed and replaced with fresh selective medium. Transfected clones were visible with the naked eye ten days later.

The presence of human antibody in the medium of wells containing gpt+ transfectants was measured using conventional enzyme linked immunosorbent assay (ELISA) techniques. Wells of a microtitre plate (Immolon, Dynatech, Chantilly, Va.) were coated with 100 ng goat anti-human IgG antibodies (SeraLab, Crawley Down, U.K.) in 100 µl 50 mM carbonate buffer pH9.6. After washing with PBST (Phosphate buffered saline pH 7.2 containing 0.05% Tween 20) culture medium in 100 µl PBST (5–50 µl) was added to each well for one hour at 37° C. The wells were then emptied, washed with PBST and 100 µl of 1:1000 dilution peroxidase conjugated goat anti-human kappa constant region antibodies (SeraLab, Crawley Down, U.K.) were added for one hour at 37° C. The wells were emptied, washed with PBST and 100µl OPD substrate buffer (400 µg/ml Q-phenylenediamine in 24 mM citrate/42 mM sodium phosphate pH 5. and 0.0003% (v/v) $H_2O_2$) was added. The reaction was stopped after a few minutes by the addition of 12.5% $H_2SO_4$ (25 µl) and the absorbance at 492 nm was measured.

The antibody secreting cells were expanded and antibody was purified from the culture medium by protein A affinity chromatography as described by Harlow and Lane (*Antibodies: A Laboratory Manual*, Cold Spring Harbor Laboratory, Cold Spring Harbor, N.Y.), the contents of which is expressly incorporated by reference.

Figure 3:
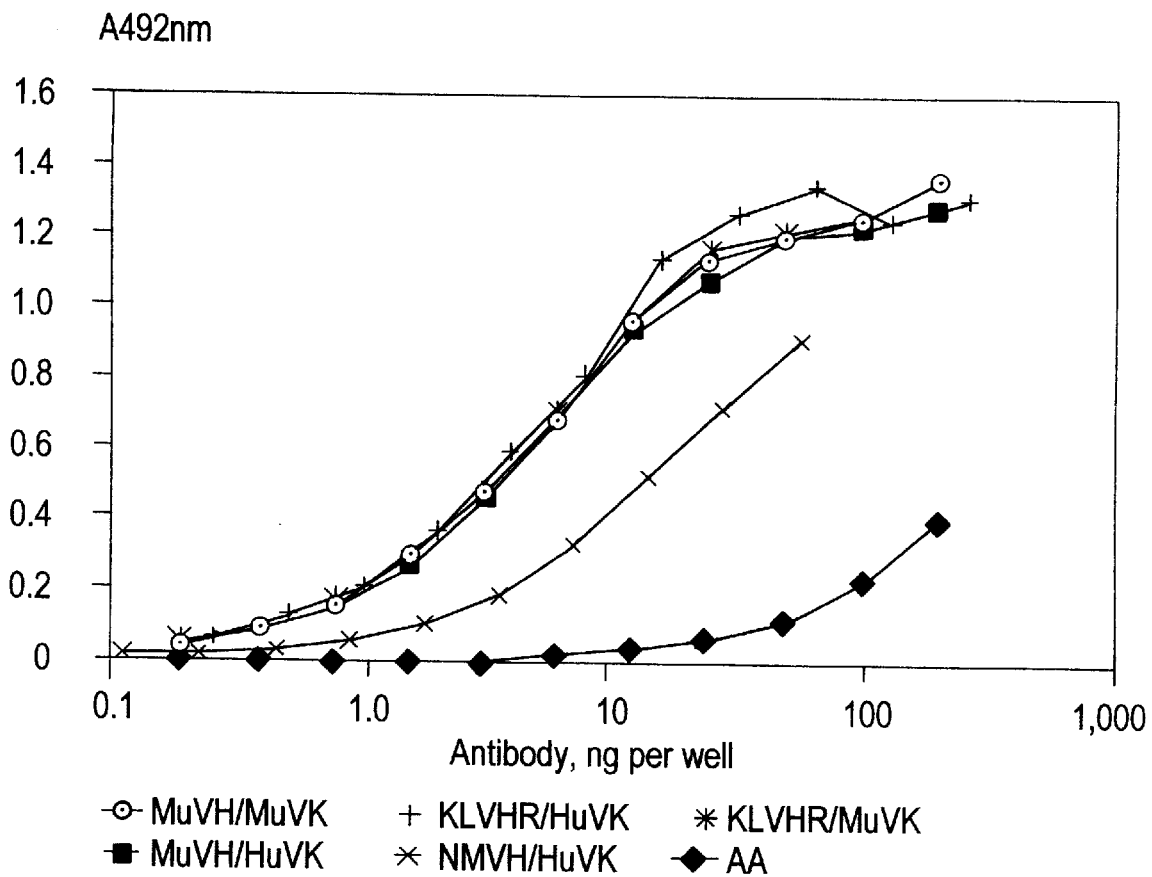
FIG. 3 depicts the binding of the test antibodies in the enzyme liked immunoassay described in the Example 1.

The binding of the antibodies to antigen was measured by ELISA. Wells of a microtitre plate (Immunlon 1, Dynatech, Chantilly, Va.) were coated with 200 ng goat anti-human IgM antibodies (Sera-lab, Crawley Down, U.K.) in 100 µl 50 mM carbonate buffer pH 9.6 at 37° C. for at least one hour. Wells were emptied and washed once with PBST and blocked with 1% BSA in PBS at room temperature for thirty minutes. The wells were emptied and washed with PBST and Cos supernatant containing FcRI/IgM fusion protein was added and incubated for one hour at room temperature. Wells were then emptied and washed three times with PBST and test antibodies diluted in 1% BSA/PBS were added and incubated for one hour at room temperature. In addition, each well contained 2 µg human IgGI, lambda antibody (Sigma, Poole, U.K.) The wells were then emptied, washed three times with PBST and 40 ng peroxidase goat anti-human kappa constant region antibodies (Sera-Lab, Crawley Down, U.K.) in 100 µl 1% BSA/PBS added to each well. After incubation for one hour at room temperature, the wells were emptied, washed three time with PBST and 10 µl HPD substrate buffer was added. The reaction was stopped by the addition of 25 µl of 12.5% $H_2SO_4$ to each well. The absorbance at 492 nm was measured and is depicted in FIG. 3. The test antibodies were the antibody containing irrelevant CDRs (AA), the fully humanized KOL/REI based antibody (KLVHR/HuVK), the mix and match derivatives of the humanized antibody (KLVHR/MuVK and MuVH/HuVK), the humanized NEWM/RBI based antibody (NMVK/HuVK) and the chimeric antibody (MuVH/MuVK).

Example 2

Production of Bispecific Antibody Comprising Antibodies Specific for an Fc Receptor and an Anti-her 2 neu Antibody Monoclonal Antibodies The anti-FcγRI mAbs, M22, M32.2 and 197 were purified from hybridoma supernatant by ion exchange chromatography and DZ33, a human anti-HIV-1 IgG1 mAb, was purified from hybridoma supernatant by protein A affinity chromatography (Pharmacia, Piscataway, N.J.) and gel filtration. M32.2 was deposited at the American Type Culture Collection, , 10801, University Blvd, Manassas Va. 20110, on Jul. 1, 1987 and has been designated with ATCC Accession No. HB9469.

Cell Lines

The murine myeloma NSO (ECACC 85110503) (ECACC, Salisbury, Wiltshire SP40JG, U.K.) a non-Ig synthesizing line and was used for the expression of recombinant mAbs. NSO cells were cultivated in DMEM plus 10% fetal bovine serum (FBS, Gibco, Paisley, U.K.). SKBR-3 is a human breast carcinoma cell line which overexpresses the HER2/neu protooncogene (ATCC, Manassas, Va.) and was cultivated in Iscove's Modified Dulbecco's Medium (IMDM, Gibco, Grand Island, N.Y.). U937 is a monocytoid cell line that expresses FcγRI and was obtained from ATCC and grown in RPM-1640 plus 10% FBS (Gibco, Grand Island, N.Y.).

Cloning Murine Immunoglobulin V Region Genes

Cytoplasmic RNA from the murine hybridoma 22 was prepared as described in Favaloro et al. (Favaloro, J., R. Treisman and R. Kamen (1982) Transcription maps of polyoma-specific RNA: analysis by two-dimensional S1 gel mapping. *Meth. Enzymol.* 65:718). The Ig V region cDNAs were made form RNA via reverse transcription initiated from primers CG1FOR, (SEQ ID NO:5) 5'-GG AAGCTTAGACAGATGGGGGTGTCGTTTTG, (encoding amino acids 115–122 of the murine IgG1 CH1 domain and a Hind III site) and CK2 FOR, (SEQ ID NO:10) 5'-GGAAGCTTGAAGATGGATACAGTTGGTGCAGC, (encoding amino acids 1–118 of the murine kappa constant domain and a Hind III site). The cDNA synthesis was performed under standard conditions using 100 U MMLV reverse transcriptase (Life Technologies, Paisley, U.K.). The $V_H$ and $V_K$ cDNAs were amplified by PCR, (Orlandi, R., D. H. Güssow, P. T. Jones and G. Winter (1989) (Cloning immunoglobulin variable domains for expression by the polymerase chain reaction), *Proc. Natl. Acad. Sci. USA* 86:3833), using the cDNA primers in concert with SH2BACK, (SEQ. ID. NO:9) 5'-T GGAATTCATGRACTTCDGGYTCAACTKRRTTT (encoding a consensus sequence of amino acids −20 to −12 of some $V_H$ signal peptides and an EcoR I site) and VK7BACK, (SEQ. ID. NO:14) 5'-TTGAATTCGGAGCTGATGGGAACATTGTAATG (encoding amino acids −4 to −1 of the signal peptide and residues 1–4 of some murine $V_K$ domains and an EcoR I site). Amplified $V_H$ and $V_K$ DNA were purified, cloned into M13, and sequenced by the dideoxy method using T7 DNA polymerase (Pharmacia, Piscataway, N.J.).

Construction of Chimeric Antibody Genes

To facilitate cloning of murine V region DNA into expression vectors, restriction sites were placed in close proximity to the termini of both M22 V region genes. For $V_H$, a 5' PstI site and a 3' BstEII site were introduced into a cloned murine VH gene by PCR using VH1BACK and VH1FOR (Id.). For $V_K$ a 5' PvuII site and a 3' Bgl II site were introduced into a cloned murine $V_K$ gene by PCR using primers VK1BACK and VK1FOR (Id.). In some instances, these primers changed one or more amino acids from those naturally occurring (see FIG. 1). These V region genes (ChVH and ChVK) were cut with the appropriate restriction enzymes and cloned into M13VHPCR1 and M13VKPCR1 (Id.) which contain an Ig promoter, signal sequence and splice sites. The DNA were excised from M13 as HindIII-BamHI fragments and cloned into the expression vectors pSVgpt and pSVhyg containing human IgG1, (Takahashi, N. et al., (1982), Structure of human immunoglobulin gamma genes: implications for evolution of a gene family, *Cell*, 29:671), and human kappa constant, (Hieter, R. A. et al., (1980) Cloned human and mouse kappa immunoglobulin constant and J region genes conserve homology in functional segments, *Cell* 22:197), region genomic DNA.

Construction of humanized Antibody Genes

Two humanized heavy chains were constructed and were based on human $V_H$s of NEWM, (Poljak, R. J. et al., Amino acid sequence of the $V_H$ region of a human mycloma immunoglobulin, (IgG New), *Biochemistry*, 16:3412), and $KOL$,(Marquat, M. et al., (1980) Crystallographic refinement and atomic models of the intact immunoglobulin molecule Kol and its antigen-binding fragment at 3.0A and 1.9A resolution, *J Mol. Biol.* 141:369. The humanized light chain was derived from the human Bence-Jones protein REI, (Epp, O. et al, (1974) Crystal and molecular structure of a dimer composed of the vandible portion of the Bence-Jones protein REI, *Eur. L Biochem.* 45:513), with some framework region (FR) changes. The modifications were made to make the $V_K$ domain more typical of human subgroup I, and included replacement of Thr39, Leu104, Gln105 and Thr107 with Lys39, Val104, Glu105 and Lys107. In addition, Met4 was changed to Leu4 to accommodate a PvuII restriction site.

DNA containing the NEWM $V_H$ and REI $V_K$ FRs with irrelevant CDRs were cloned into the vectors M13VHPCR1 and M13VKPCR1 (Favaloro et al. Supra). DNA encoding the KOL $V_H$ was constructed by a series of sequential PCRs, using oligodeoxyribonucleotides encoding KOL FR amino acids and irrelevant CDRs. The constructs were then cloned into M13 VHPCR1.

Oligodeoxyribonucleotides were synthesized to encode the mAB M22 CDRs which were flanked by nucleotides corresponding to the human FRs. For the humanized VH based on NEWM, the primers included murine FR amino acids Phe27, Ile28 and Arg71 since these were likely to influence antigen binding, (Chothia, C. and A. M. Lesk (1987), Canonical structures for the hypervariable regions of immunoglobulins, *J. Mol Biol.*, 196:901; Tramontano, A. et al., (1990), Framework residue 71 is a major determinant of the position and conformation of the second hypervariable region in $V_H$ domains of immunoglobulins, *J. Mol. Biol.*, 215:175). For the humanized V., murine amino acid Phe71 was similarly included as a residue capable of affecting affinity, (Foote, J. and G. Winter, (1992), Antibody framework residues affecting the conformation of the hypervariable loops, *J. Mol. Biol.* 224:487. No murine FR residues were included in the KOL $V_H$. Oligodeoxyribonucleotides were 5'-phosphorylated and with the M13 universal forward primer annealed to the human V region genes cloned in M13 in reactions containing M13 ssDNA template. The DNA was extended and ligated with 2.5 U T7 DNA polymerase (United States Biochemicals, Cleveland, Ohio) and 0.5 U T4 DNA ligase (Gibco BRL, Grand Island, N.Y.). The mutated strand was preferentially amplified from the extension/ligation mixture using M13 reverse sequencing primer with 1 U Vent DNA polymerase (New England Biolabs, Beverly, Mass.) and was then amplified by PCR using both M13 forward and reverse primers. Product DNA was cut with BamH1 and HindIII, cloned into M13 and triple CDR-grafted mutants identified by DNA sequencing.

M13 clones containing the humanized V regions were sequenced in their entirety to ensure the absence of spurious mutations. RF DNA from the confirmed clones was digested with HindIII and BamHI, cloned into pSVgpt or pSVhyg and human IgG1 or human kappa constant regions added exactly as described for the construction of the chimeric antibody genes.

Expression and Purification of Recombinant mAbs

Heavy (5 µg) and light (10 µg) chain expression vectors were digested with PvuI, ethanol precipitated and dissolved in 50 µl water. NSO cells ($1-2 \times 10^7$) were harvested by centrifugation, resuspended in 0.5 ml DMEM and mixed with the DNA in a 0.4 cm electroporation cuvette. After 5 min. on ice the cells were given a single pulse of 170 V, 960 µF (GenePulser, Bio-Rad, Melville, N.Y.) and incubated further for 15 min. on ice. The cells were allowed to recover in DMEM for 24–48 hours. The medium was then made selective by the addition of mycophenolic acid (0.8 ug/ml) and xanthine (250 µg/ml). Aliquots of 200 µl were distributed into 96-well plates. After a further 10–12 days, cells from the wells containing the highest levels of antibody measured by ELISA were selected and cloned by limiting dilution.

Antibodies were purified from overgrown cultures by protein A affinity chromatography (Boehringer Mannheim, Lewes, U.K.) Concentrations were determined by measuring $A_{280nm}$ and confirmed by ELISA and SDS-PAGE.

ELISA for Measurement of antibody Binding

The wells of a microtiter plate were coated with goat anti-human IgM antibodies (Sera-Lab, Crawley Down, U.K.) in 50 mM bicarbonate buffer, pH 9.6. The plate was blocked with 1% BSA and followed by the addition of a soluble fusion protein consisting of the extracellular domain of human FcγRI and human IgM heavy chain (sFcγRI-µ) obtained from transiently transfected COS cells (the expression vector was kindly provided by Dr. Brian Seed, Massachusetts General Hospital, Boston, Mass.). Recombinant 22 or control mAbs were then added in the presence of excess (2.2 µg/well) human IgG1 antibodies (Sigma, St. Louis, Mo.) that contained λ light chains to block the non-specific binding of the test mAbs via their Fc portion. Bound 22 mAbs were detected with peroxidase-labeled goat anti-human kappa chain antibodies (Sera-Lab, Crawley Down, U.K.) and o-phenylenediamine.

Fluoresceination of Antibodies

The pH of mAb solution was adjusted to 9.3 by the addition of 0.1M $Na_2CO_3$.

Fluorescein iso-thiocyanate (FITC) (Sigma, St. Louis, Mo.) was dissolved in DMSO at a concentration of 2 mg/ml. Forty µg of FITC was added for each milligram of mAb and incubated for two hours at room temperature. The fluoresceinated mAb was separated from the free FITC by G-25 chromatography.

Preparation of Blood Cells

Buffy coats were prepared from heparinized whole venous blood. Whole blood was diluted with RPMI containing 5% dextran at a ratio of 2.5:1 (v/v). The erythrocytes were allowed to sediment for 45 minutes on ice, then the cells in the supernatant were transferred to a new tube and pelleted by centrifugation. The residual erythrocytes were removed by hypotonic lysis. The remaining lymphocytes, monocytes and neutrophils were kept on ice until use in binding assays. For some experiments, neutrophils were separated from mononuclear cells by ficoll hypaque (Pharmacia, Piscataway, N.J.) gradient separation. To up-regulate FcγRI, neutrophils and mononuclear cells were treated with cytokines. Cultures of mononuclear cells were incubated at 37° C., 5% $CO_2$ for 48 hours in teflon dishes at $4 \times 10^6$ cells/ml of RPMI containing 2.5% normal human serum type AB (Sigma, St. Louis, Mo.) and 500 IRU/ml IFN-γ (R&D Systems, Minneapolis, Minn.). Neutrophils were cultured for 48 hours (37° C., 5% $CO_2$) in AIM V media (Gibco, Grand Island, N.Y.) with 50 ng/ml G-CSF (Kindly provided by R. Repp, U. of Erlanger, Germany) and 500 IRU/ml IFN-γ.

Flow Cytometry

Cell binding assays were performed using 96-well microtiter plates as previously described, (Guyre, P. M. et al., Monoclonal antibodies that bind to distinct epitopes on FcγR are able to trigger receptor function. *J. Immunol.*, 143:1650). Briefly, cells were washed in PBS, pH 7.4 containing 2 mg/ml BSA and 0.05% $NaN_3$ (PBA), and adjusted to $2.0 \times 10^7$ cells/ml with PBA. FITC-labeled and unconjugated antibodies were prepared in PBA. Cells (25 μl), antibodies (25 μl) and human serum (25 μl), or human IgG (10 mg/ml, Sigma, St. Louis, Mo.) (25 μl), or PBA (25 μl) were added to the microtiter plate, and left on ice for 45–60 minutes. Unbound antibody was removed from the wells by washing the cells 3 times with PBA. The cells were fixed with 1% paraformaldehyde. Cell associated fluorescence was analyzed on a Becton Dickinson FACScan.

BsAb Coupling Procedure

BsAb were constructed using the method of Glennie et al, (Glennie, M. J. et al., (1987), Preparation and performance of bispecific F(ab' gamma)$^2$, antibody containing thioether-linked Fab' gamma fragments, *J. Immunol.*, 139:2367. mAbs 22 (both murine and humanized) and 520C9 (anti-HER2/neu) antibodies were produced by in vitro cultivation of the respective hybridoma cells. The antibodies were separately digested with pepsin to F(ab')$_2$, and subsequently reduced to Fab' by addition of 10 mM mercaptoethanolamine (MEA) for 30 minutes at 30° C. The Fab' fragments were applied to a Sephadex G-25 column equilibrated in 50 mM Na Acetate, 0.5 mM EDTA, pH 5.3 (4° C.). Orthophenylenedimaleimide (o-PDM, 12 mM) dissolved in dimethyl formamide and chilled in a methanol/ice bath was added (one half volume) to the murine 22 Fab' in the case of M 22×520C9, and to 520C9 Fab' in the case of H 22×520C9 and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the M22Fab'-maleimide was added to the 520C9 Fab' or the 520C9 Fab'-maleimide was added to H22 Fab' at a 1:1 molar ratio. The reactants were concentrated under nitrogen to the starting volume using a Diaflo membrane in an Amicon chamber (all at 4° C.). After 18 hours the pH was adjusted to 8.0 with 1M Tris-HCl, pH 8.0. The mixture was then reduced with 10 mM MEA (30 minutes, 30° C.) and alkylated with 25 mM iodoacetamide. The bispecific F(ab')$_2$ was separated from unreacted Fab's and other products by a Superdex 200 (Pharmacia, Piscataway, N.J.) column equilibrated in PBS.

Antibody Dependent Cellular Cytotoxicity (ADCC)

The HER2/neu over-expressing human breast carcinoma cells, SKBR-3, were used as targets for lysis by cytokine activated neutrophils (see preparation of blood cells). Targets were labeled with 100 μCi of $^{51}$Cr for 1 hour prior to combining with neutrophils and antibodies in a U-bottom microtiter plate. After incubation for 5 hours at 37° C. supernatants were collected and analyzed for radioactivity. Cytotoxicity was calculated by the formula: % lysis= (experimental CPM−target leak CPM/detergent lysis CPM−target leak CPM)×100%. Specific lysis=% lysis with antibody−% lysis without antibody. Assays were performed in triplicate.

Superoxide Induction

U937 cells were used for measuring the ability of H22 to trigger a superoxide burst via FcγRI, (Pfefferkom, L. C. and G. R. Yeaman (1994), Association of IgA-Fc receptors (FcxR) with Fcε RIγ 2 subunits in U937 cells, *J. Immunol.* 153:3228, Hallet, H. B. and A. K. Campbell (1983). Two distinct mechanisms for stimulating of oxygen−radical production in polymorphonuclear leucocytes, *Biochem J.* 216:459). U937 cells were cultured for five days in RPMI-1640 (Gibco, Grand Island, N.Y.) with 10% FBS (Hyclone, Logan, Utah) in the presence of 100 U/ml IFN-γ (Genentech, S. San Francisco, Calif.) to induce differentiation and increased expression of FcγRI. On the day of the experiment, these differentiated cells were incubated for 20 minutes in fresh RPMI-1640 with 10% FBS at 37° C. The cells were then pelleted and resuspended at a concentration of $3 \times 10^6$ cells/ml in PBS supplemented with 1 mM $CaCl_2$, 1 mM $MgCl_2$, 11 mM glucose, and 100 μg/ml BSA (Sigma, St. Louis, Mo.). To trigger the release of superoxide, 100 μl of cells were added to 100 μl of a reaction solution containing 0.1 mM luminol (Sigma, St. Louis, Mo.), 0.5 mM sodium vanadate (Sigma, St. Louis, Mo.), and either mAb M22, H22, or 197 and placed in the luminometer at 22° C. Measurements of the spontaneous production of superoxide were made every 30 to 40 seconds starting immediately following the addition of the cells to the reaction solution in the luminometer. To compare the superoxide triggered by crosslinking FcγRI with M22, H22 or 197, each mAb was used at a concentration of 10 μg/ml. The production of superoxide in mV/sec was monitored for 20 minutes. MAb M22, M32.2 and 197 were added at various concentrations to establish the dose-responsiveness of superoxide production.

Results

Murine Ig V Region Genes

Ig V region cDNAs were prepared from M22 hybridoma RNA using primers specific for murine heavy and kappa constant regions and were amplified by PCR with the additional use of a series of primers based on sequences of known signal and/or 5' sequences of mature V regions. PCR products of the expected sizes for $V_H$ and $V_κ$ were obtained using the SH2BACK/CG1FOR and VK7BACK/CK2 FOR primer combinations. Amplified DNA was digested with appropriate restriction enzymes, cloned into M13 and the sequence in both directions determined from at least 24 independent clones. The deduced amino acid sequences are shown in SEQ. ID Nos. 29 and 30. The 4 N-terminal residues of $V_κ$ are encoded by the VKBACK primer.

The M22 $V_H$ and $V_{78}$ are members of murine heavy chain subgroup IIID and kappa subgroup 1, (Kabat, E. A. et al., (1991), *Sequences of Proteins of Immunological Interest*, 5 th Ed., U.S. Department of Health and Human Services), respectively. Apart from the residue at L97, the amino acid sequence of the M22 $V_κ$ is identical to that from the murine anti-IgG mAb A17 (Shlomchik, M. et al., Variable region sequences of murine IgM anti-IgG monoclonal autoantibodies (rheumatoid factors). II Comparison of hybridonias derived bylipopolysaccharide stimulation and secondary protein immunization, *J. Exp. Med.* 165:970).

Humanized mAbs and Initial Characterization of their Binding

M22 VH FR showed greater homology (79%) to KOL (human subgroup III) than to NEWM (57%) (human subgroup II). To see how this difference might affect binding, heavy chains were constructed based either on NEWM $V_H$ including the murine residues Phe27, Ile28 and Arg71, or on KOL $V_H$ with no murine FR amino acids. Both humanized $V_H$ were partnered with the same REI-derived humanized light chain.

The affinity of the humanized mAbs was initially assessed by ELISA measuring the binding to FcγRI/IgM heavy chain fusion protein. The data showed that the KOL $V_H$/REI $V_K$ mAb had the same binding as the chimeric mAb whereas the NEWM $V_H$/REI $V_K$ mAb exhibited an approximate 5-fold lower affinity. The low binding of a nonspecific human IgG1 mAb showed that>95% of binding of the humanized mAbs was via the Fv portion rather than through the Fc domain.

While additional changes to the NEWM FR would be expected to restore binding affinity these could create novel epitopes which might provoke an unwanted immunological response. We therefore chose the KOL $V_H$/REI $V_K$ mAb, designated H22, for a further examination of its binding characteristics.

Functional Characterization of mAbH22

A series of binding experiments were performed to establish the specificity and isotype of the H22 antibody. Peripheral blood leukocytes stained with fluorescein-conjugated M22 or H22 demonstrated specific binding to monocytes with approximately $10^4$ binding sites per cell. In contrast, lymphocytes or unstimulated neutrophils had little or no specific binding (Table 1):

TABLE 1

Specific Binding of H22 to Monocytes

| Antibody | Monocytes | Lymphocytes | PMNs |
| --- | --- | --- | --- |
| M22 | 10,000[a] | <1000 | <1000 |
| H22 | 10,500 | <1000 | <1000 |

[a]Antibody sites per cell, average of duplicates

To demonstrate that the H22 binds to FcγRI at the same site as M22 and that it also binds as a ligand at the Fc binding domain, competition experiments with two anti-FcγRI murine mAb (M22 and M32.2) and a human IgG1 mAb were performed. Uncojugated H22 and M22 competed equivalently for either the binding of fluorescinated M22 or fluoresceinated H22 in the presence of excess human IgG which saturated the Fc binding sites on FcγRI. As expected, the anti-FcγRI antibody M32.2 which binds to a different site on FcγRI than M22 (Guyre, P. M. et al., *J. Immunol.* 143:1650) was also unable to compete with the M22-FITC. In addition, the inhibition of H22-FITC by H22 and not by an irrelevant human IgG1 mAb confirmed the specificity of FcγRI binding via the V regions of H22.

H22, but not M22, was able to compete for Fc mediated binding to FcγRI by a fluoresceinated human IgG1. This experiment demonstrated that the Fc portion of H22 but not M22 bound to the Fc binding domain of FcγRI. This is consistent with the ability of the Fc portion of human IgG1 antibodies, but not murine IgG1, to bind FcγRI with high affinity.

Since the humanization of M22 was primarily to increase its immunotherapeutic potential, the binding activity of H22 to monocytes and cytokine-activated neutrophlils was determined in the presence of human serum. H22-FITC bound with similar affinity to FcγRI on monocytes in the presence or absence of human serum. In contrast, the Fc-mediated binding of an irrelevant human IgG-FITC was completely inhibited by human serum. Likewise, H22-FITC bound with similar affinity to IFN-γ-treated neutrophils in the absence and in the presence of human serum. Collectively, the data demonstrated that H22 binds both via its V regions to a site distinct from the Fc binding domain and via its Fc region to the ligand binding domain of FcγRI. The former binding activity effectively overcomes antibody blockade of human IgG1.

Functional Activity ofl H22 BsAb

The foremost application of anti-FcγRI antibodies for immunotherapy is the development of BsAbs which link FcγRI-bearing effector cells to a tumor cell, a virus, or a virally-infected cell. Such BsAb have been developed with M22; therefore, a comparison was made of the ability of the M22 anti-tumor BsAb (520C9xM22) and a corresponding H22 BsAb (520C9xH22) to mediate cytotoxicity. These BsAbs consisted of H22 or M22 Fab' chemically conjugated to the Fab' of an anti-HER2/neu antibody (520C9), and thus were specific for the effector cell trigger molecule FcγRI and the tumor antigen.

Comparison of M22-derived and H22-derived BsAbs was done by ADCC assays. M22- and H22-derived BsAbs mediated the killing of HER2/neu overexpressing SKBR-3 cells. Both the murine and humanized BsAbs exhibited similar levels of lysis of antigen bearing target cells. In addition, both BsAb retained ADCC activity in the presence of human serum, while excess M22 F(ab')$_2$ resulted in complete inhibition of killing. Taken together these results show that the H22 BsAb-induced lysis is mediated through the M22 epitope and that the ADCC is FcγRI specific.

Finally, the ability of H22 and M22 to stimulate superoxide production by the monocyte-like cell line U937 was evaluated. M22, which binds to the FcγRI only by its V regions, induced a very low level oxygen burst, presumably because it is unable to cross-link the receptor efficiently. However, H22, which can cross-link FcγRI by binding as a ligand via its Fc domain and, additionally, as an antibody via its Fv, induced a more substantial release of superoxide.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A humanized antibody comprising:
an antigen binding region which binds to the human high affinity Fc receptor FcγRI for human immunoglobulin G, wherein the antigen binding region comprises all complementary determining regions (CDRs) from the heavy and light chains of a non-human antibody specific for a human Fc receptor, and
variable domain framework regions from the heavy and light chains of a human antibody, wherein the heavy chain variable region comprises the amino acid sequence of SEQ ID NO: 2, and the light chain variable region comprises the amino acid sequences of SEQ ID NO: 4.

2. The humanized antibody of claim 1, wherein the antigen binding region binds to the human high affinity Fc receptor FcγRI at a site which is not blocked by human immunoglobulin G.

3. The humanized antibody of claim 2, wherein the complementarity determining regions are derived from a monoclonal antibody selected from the group consisting of mab 32.2 produced by the hybridoma having ATCC Deposit Number HB 9469 and mab 22 produced by the hybridoma having ATCC Deposit Number HB 12147.

4. The humanized antibody of claim 3, wherein the variable domain framework regions from the heavy chain of the human antibody are derived from a protein selected from the group consisting of KOL and NEWM.

5. The humanized antibody of claim 4, wherein the variable domain framework region from the light chain of the human antibody are derived from the human protein REL.

6. A bifunctional molecule, comprising the humanized antibody of claim 3 or an antigen binding fragment thereof, and an antigen binding region specific for an antigen present on a target cell.

7. The bifunctional molecule of claim 6, wherein the target cell is a cancer cell.

8. The bifunctional molecule of claim 7, wherein the cancer cell is a breast or ovarian cancer cell.

9. The bifunctional molecule of claim 6, wherein the antigen is HER 2/neu.

10. The humanized antibody of claim 1 produced by the cell line having ATCC Accession Number CRL 11177.

11. A bifunctional molecule, comprising the humanized antibody of claim 1 or an antigen binding fragment thereof, and an antigen binding region specific for an antigen present on a target cell.

12. The bifunctional molecule of claim 11, wherein the target cell is a cancer cell.

13. The bifunctional molecule of claim 12, wherein the cancer cell is breast or ovarian cancer cell.

14. The bifunctional molecule of claim 11, wherein the antigen is HER 2/neu.

15. The bifunctional molecule of claim 11, wherein the antigen comprises a component from an infectious agent.

16. The bifunctional molecule of claim 15, wherein the infectious agent is hepatitis or human immunodeficiency virus.

17. The bifunctional molecule of claim 11, wherein the target cell is an antibody-producing cell.

18. A humanized antibody specific for a human Fc receptor for human immunoglobulin G comprising a heavy chain variable region comprising the amino acid sequence shown in SEQ ID NO: 1, and a light chain variable region comprising the amino acid sequence shown in SEQ ID NO: 4.

19. A humanized antibody specific for a human Fc receptor for human immunoglobulin G comprising a heavy chain variable region comprising the amino acid sequence shown in SEQ ID NO: 2, and a light chain variable region comprising the amino acid sequence shown in SEQ ID NO: 4.

20. A bispecific molecule comprising a humanized anti-FcγRI antibody or an antigen binding fragment thereof produced by a cell line having an ATCC accession number CRL1177, and an anti-Her-2/neu monoclonal antibody (520C9) or an antigen binding fragment thereof produced by a hybridoma cell line having ATCC accession number HB 8696.

* * * * *

UNITED STATES PATENT AND TRADEMARK OFFICE
CERTIFICATE OF CORRECTION

PATENT NO. : 6,500,931 B1 Page 1 of 1
DATED : December 31, 2002
INVENTOR(S) : Philip R. Tempest et al.

It is certified that error appears in the above-identified patent and that said Letters Patent is hereby corrected as shown below:

<u>Title page,</u>
Item [30], Foreign Application Priority Data, insert
-- November 2, 1993 (PCT) PCT/US93/10384 --.

Signed and Sealed this

Ninth Day of March, 2004

JON W. DUDAS
*Acting Director of the United States Patent and Trademark Office*